United States Patent [19]

Boron

[11] Patent Number: 4,875,380
[45] Date of Patent: Oct. 24, 1989

[54] CORRUGATED JACKET FOR MOLTEN METAL SAMPLER

[75] Inventor: Joseph J. Boron, Medina, Ohio

[73] Assignee: Midwest Instrument Co., Inc., Hartland, Wis.

[21] Appl. No.: 136,849

[22] Filed: Dec. 22, 1987

[51] Int. Cl.⁴ .............................................. G01N 1/12
[52] U.S. Cl. ............................ 73/864.58; 73/864.53; 73/864.59
[58] Field of Search ......... 73/864.58, 864.59, DIG. 9, 73/864.53

[56] References Cited

U.S. PATENT DOCUMENTS

| | | |
|---|---|---|
| 3,455,164 | 7/1969 | Boyle . |
| 3,481,201 | 12/1969 | Falk . |
| 3,805,621 | 4/1974 | Falk ............................ 73/DIG. 9 X |
| 3,816,183 | 6/1974 | Kraus .................................... 136/234 |
| 3,967,505 | 8/1976 | Feichtinger ................ 73/DIG. 9 X |
| 3,996,803 | 12/1976 | Falk . |
| 4,046,016 | 9/1977 | Hackett ........................ 73/864.58 X |
| 4,358,630 | 11/1982 | Falk ................................ 374/139 X |
| 4,396,792 | 8/1983 | Falk ...................................... 136/234 |
| 4,499,777 | 2/1985 | Hackett ........................ 73/864.58 X |
| 4,521,639 | 6/1985 | Falk ...................................... 136/234 |
| 4,603,590 | 8/1986 | Staats et al. ...................... 73/864.58 |

Primary Examiner—Tom Noland
Attorney, Agent, or Firm—Fuller, Puerner & Hohenfeldt

[57] ABSTRACT

Disclosed herein is a molten metal sampler with a wrap of corrugated board with flutes which provide vertical channels for conveying and outgasing the gas caused by reaction of the body of a molten metal sampler or immersion thermocouple in the molten metal to above the surface of the metal to prevent splash of the equipment operators. The corrugated board is coated with a refractory cement to protect the corrugated board during immersion to maintain the integrity of the channels.

3 Claims, 1 Drawing Sheet

U.S. Patent    Oct. 24, 1989    4,875,380
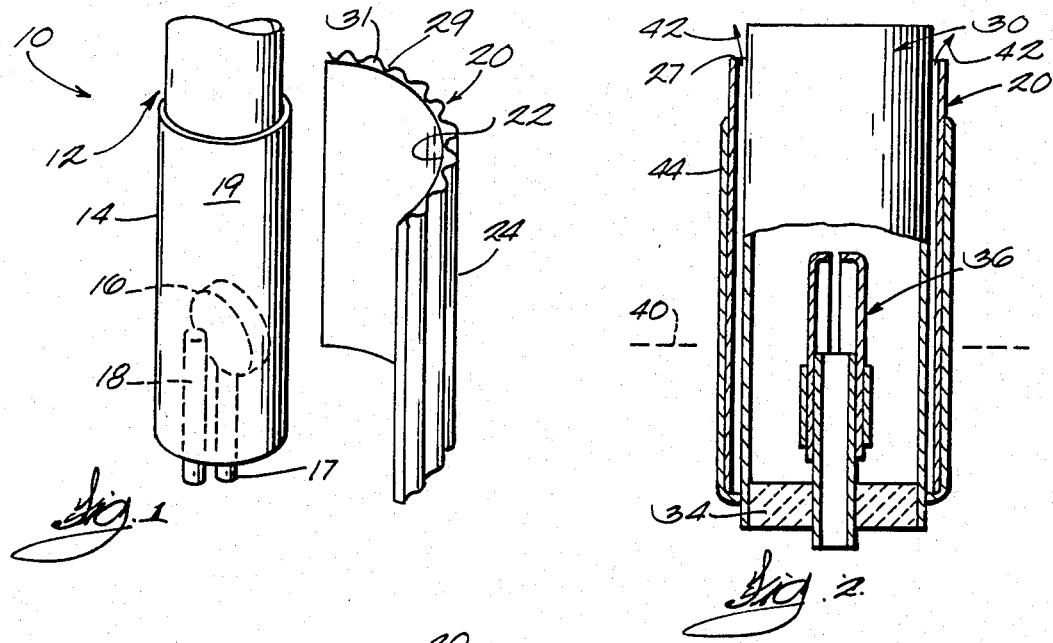
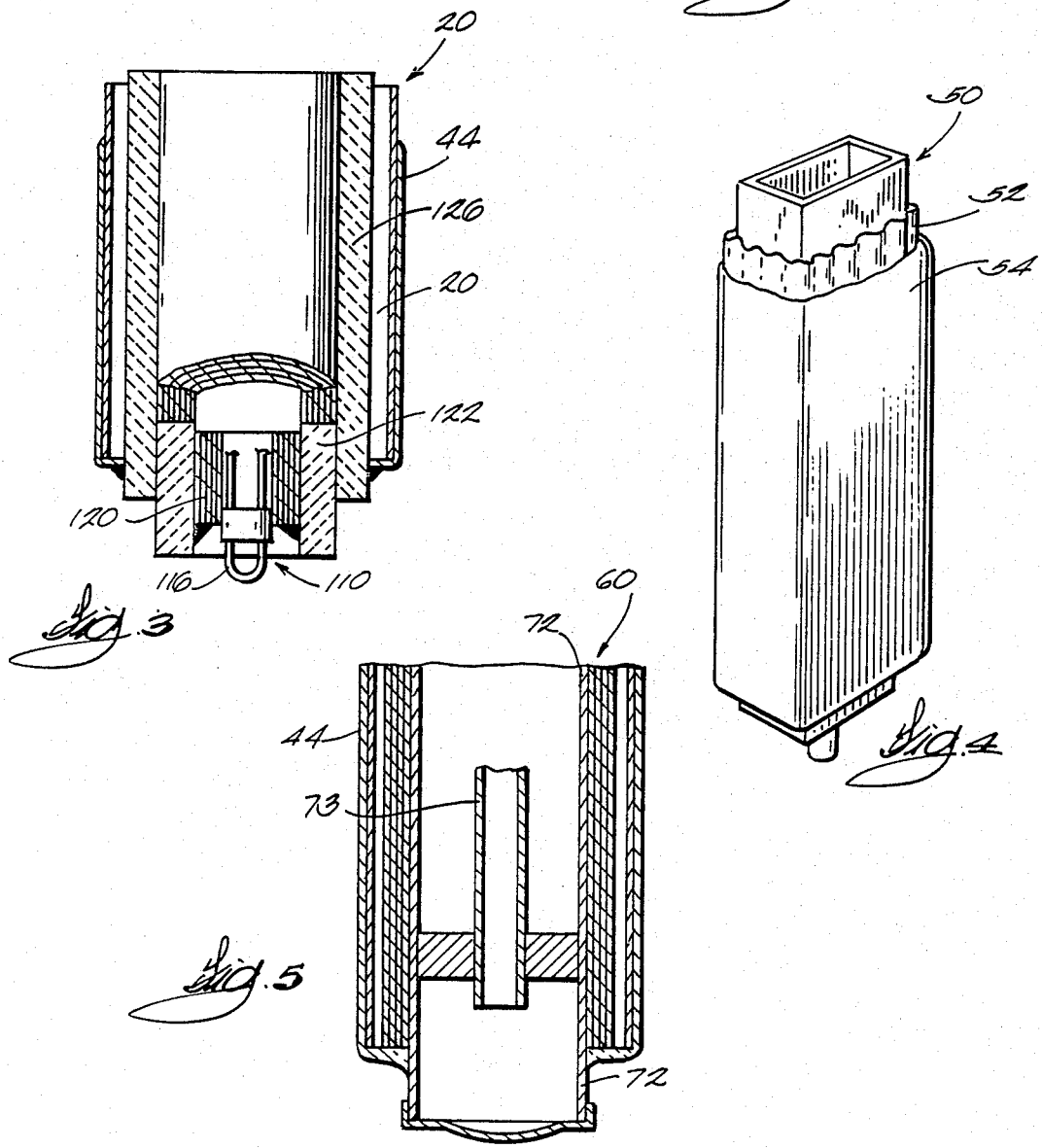

CORRUGATED JACKET FOR MOLTEN METAL SAMPLER

FIELD OF INVENTION

The invention relates to the art of molten metal sampling using immersion vehicles for obtaining molten metal temperatures and a sample thereof.

BACKGROUND OF INVENTION

The art of sampling molten metal and obtaining temperatures with thermocouples has developed significantly since the early 1960's. In addition to various forms of sampling cartridges, sampling techniques and thermocouple lances, various improvements have been made in protecting the sampling vehicles or lances during immersion to provide sufficient immersion time to obtain a representative metal sample below the slag surface of the melt and obtain a representative bath temperature. In addition to protecting the immersion vehicle, there also is an interest in protecting the equipment operator who is taking the temperature or the sample from the splash of molten metal caused by boiling or combustion gases caused by disintegration of the sampler vehicle. The paperboard products employed to protect samplers will attain ignition or kindling temperatures but because of lack of oxygen will gasify rather than burn.

Various types of protective coatings have been employed. Wrappings of fiber coated paper have been used. The gasification or combustion of the paper causes some splash and boiling as the paper is consumed. A further protective coating employed in the art is a fiberglass tape wrapped over a coating of refractory cement. Fiberglass tape depends on its strength to prevent blowing off of portions of the wrap and splash molten metal. This technique is expensive and also includes fibers which are discouraged from use in some countries because the fibers are regarded as a health hazard. Other types of protective coverings include vacuum formed fiber sleeves. These coverings are expensive and include the undesirable fiber. A further protective coating involves a coating of ceramic bonded onto a steel tube. This does not outgas and there is no reaction. It is also the most expensive. Moreover, when used with thermocouples, it conducts heat into the cold junction of the thermocouple area and can damage the thermocouple, provide poor performance and afford a limited life of the thermocouple.

It has been common to use one or more cardboard sleeves or tubes to protect the sampling cartridges whether they are immersion samplers illustrated in U.S. Pat. No. 3,481,201 or a stream sampler such as shown in U.S. Pat. No. 3,996,803. Examples of refractory fiber protection is found in U.S. Pat. Nos. 4,521,639 and 3,816,183. U.S. Pat. No. 4,396,792 is a further example of a precast refractory fiber sleeve.

U.S. Pat. No. 3,455,164 shows a metal tube wrapped with a ceramic impregnated asbestos fiber.

SUMMARY OF INVENTION

The invention provides a corrugated board jacket for an immersion sampler or thermocouple assembly to eliminate the need for a fiber coating and to provide an outgas channel capability to prevent splash of molten metal. The invention provides a wrap of single face corrugated board in which the corrugated board smooth face is wrapped in contact with the exterior of the sampling vehicle and the flutes face outwardly. The wrap can be glued or otherwise secured to the immersion vehicle or sampler. A refractory cement coating over the fiber board either brushed, dipped or sprayed prevents boiling and splash of metal from the molten metal bath. The corrugations assist in accumulating and holding a thick coating of refractory cement. The refractory coating also seals and protects the openings defined by the peaks and one side and the facing of the board which provide a plurality of longitudinally extending channels which afford outgasing of gas generated during boiling of the cardboard while immersed. The flutes or corrugated board extends above the immersion line and hence allows for discharge of the gas above the surface of the molten metal rather than into the molten metal to minimize splash.

The thickness of the refractory cement coating on the exterior of the fiberboard is selected to withstand the ferrostatic pressure of the molten metal bath which depends on the depth of the intended immersion in the molten metal.

The present invention provides a protective covering for immersion vehicles which eliminates the expense of a ceramic bonded to a steel tube and the fibers associated with other types of protective jackets.

Further objects, advantages and features of the invention will become apparent from the disclosure.

DESCRIPTION OF THE DRAWINGS

FIG. 1 is an exploded perspective view of a sampler with a corrugated board wrap;

FIG. 2 is a fragmentary side elevational view of an immersion sampler;

FIG. 3 is a side elevational view of an immersion thermocouple;

FIG. 4 is a side elevational view of a sampler with a rectangular body; and

FIG. 5 is a fragmentary side elevational view of a pre-evacuated sampler.

DESCRIPTION OF PREFERRED EMBODIMENT

Although the disclosure hereof is detailed and exact to enable those skilled in the art to practice the invention, the physical embodiments herein disclosed merely exemplify the invention which may be embodied in other specific structure. The scope of the invention is defined in the claims appended hereto.

FIG. 1 shows an immersion vehicle 10 including a handle 12 supporting a sampler body 14 which can be equipped with either a molten metal sample chamber or a thermocouple. The handle 12 and the body 14 can be concentric, tightly fitted fiberboard or cardboard tubes. A molten metal sample cartridge 16 is contained in the tube with a tube 17 defining a fill passage. A thermocouple assembly 18 is also shown for taking bath temperature.

In accordance with the invention, channel means are arranged around the body 14 to afford release of gas from the combustion of the tubes below the surface of the molten metal to above the surface. In the disclosed construction in FIG. 1, the channel means comprises a wrap of single faced corrugated board 20 with a face sheet 22 which is wrapped in contact with the surface 19 of the body 14. The corrugated board is provided with a corrugated substrate 24 which is conventionally glued to the face sheet 22 by starch or other conventional paperboard adhesive. The flutes 29 define and separate gas channels 31.

The sampler shown in FIG. 2 includes a body 30 which can be a fiberboard or steel tube, which includes the wrap of fluted corrugated board 20 extending from a ceramic mount 34 which supports a metal sampler cartridge 36 such as that illustrated in U.S. Pat. No. 3,805,621, the entire patent of which is incorporated herein by reference. The top 27 of the corrugated board wrap 20 extends above the immersion line or surface level of the molten metal indicated by the line 40 to provide outgasing of gas at 42 above the surface 40. A refractory cement coating 44 is provided to protect the corrugated board wrap and maintain its integrity during immersion in molten metal to conduct the gas above the surface of the molten metal to prevent splash of the molten metal.

FIG. 3 shows a repeating use thermocouple unit 110 as disclosed in U.S. Pat. No. 4,358,63, the entire disclosure of which is incorporated herein by reference. A corrugated wrap 20 and a refractory coating 44 has been applied. The unit 110 includes a thermocouple element 116 supported in a paperboard tube 120 which is supported in further paperboard tubes 122 and 126. In U.S. Pat. No. 4,358,630 the tube 126 is refractory fiber rather than paperboard. The fluted corrugated board wrap used herein eliminates the need for the refractory fiber coating.

FIG. 4 shows a rectangular sampler body 50 also provided with the corrugated wrap 52 coated with ceramic coating 54. The flexible wrap 52 easily conforms to most sampler body shapes.

FIG. 5 shows a paperboard body 60 which supports a pre-evacuated sample cartridge 72 with a sample mold 73, similar to that shown in the U.S. Pat. No. 3,967,505, the entire disclosure of which is incorporated herein by reference.

The present invention provides a low cost, protective jacket with integral channels which achieve the objectives of the invention and eliminate the problems in the prior art. Corrugated board is exceedingly inexpensive and provides the protection required. The use of paperboard in molten metal sampling lances has been known for some time. The combustion or consumption and gasification of the corrugated board provides an insulative gas coating, such as an ablative coating used on space vehicles to enhance or increase the immersion time of immersion vehicles. Hence, it is desirable to use paperboard to provide insulation of the sample cartridge to prevent melting and destruction of the sample cartridge during the filling process of two to ten seconds. With the present invention, the same benefit heretofore recognized and employed is achieved with the corrugated board layer as well as the outgas capability with the protected channels.

I claim:

1. An immersion vehicle for studying the properties of molten metal including a vehicle body for supporting analysis apparatus and a handle for manipulating the vehicle body in molten metal, the improvement wherein said body is provided with channel means arranged along the exterior of the body to afford release of gas caused by reaction of the vehicle body with the molten metal above the immersion line in the molten metal to minimize splashing of molten metal and to protect the vehicle body and wherein said channel means comprises a wrap of corrugated board having sequential alternate peaks and valleys in which the peaks define channels which direct the gas caused by the reaction of the vehicle body with the molten metal above the molten metal surface.

2. The improvement of claim 1 in which the corrugated board is paperboard that is provided with a refractory coating to protect the channels during immersion and adequate to prevent splashing during the immersion of the vehicle body.

3. An immersion vehicle for studying the properties of molten metal including a vehicle body for supporting analysis apparatus and a handle for manipulating the vehicle body in molten metal, the improvement wherein said body is formed from a combustible tube and wherein combustion gas release means surround the exterior of the body and is spaced therefrom so as to form a substantially annular passage to release gas caused by reaction of the vehicle body with the molten metal above the immersion line in the molten metal to minimize splashing of molten metal and to protect the vehicle body.

* * * * *